(12) United States Patent
Wojak

(10) Patent No.: US 9,802,153 B2
(45) Date of Patent: Oct. 31, 2017

(54) SULPHUR-ASSISTED CARBON CAPTURE AND UTILIZATION (CCU) METHODS AND SYSTEMS

(71) Applicant: Bogdan Wojak, Vancouver (CA)

(72) Inventor: Bogdan Wojak, Vancouver (CA)

( * ) Notice: Subject to any disclaimer, the term of this patent is extended or adjusted under 35 U.S.C. 154(b) by 0 days.

(21) Appl. No.: 15/174,504

(22) Filed: Jun. 6, 2016

(65) Prior Publication Data

US 2017/0252696 A1    Sep. 7, 2017

(30) Foreign Application Priority Data

Mar. 4, 2016    (WO) ................ PCT/CA2016/050235

(51) Int. Cl.
*C25B 1/22*    (2006.01)
*C25B 1/02*    (2006.01)
(Continued)

(52) U.S. Cl.
CPC ......... *B01D 53/62* (2013.01); *B01D 53/8681* (2013.01); *C01C 1/04* (2013.01);
(Continued)

(58) Field of Classification Search
CPC ................ C25B 1/02; C25B 1/22; C25B 9/08
See application file for complete search history.

(56) References Cited

U.S. PATENT DOCUMENTS 2,813,006 A    11/1957    Hayworth et al.
2,983,580 A    5/1961    Kerr
(Continued)

FOREIGN PATENT DOCUMENTS

CA    2663131    3/2008
CA    2700746    4/2009
(Continued)

OTHER PUBLICATIONS

International Search Report dated Sep. 21, 2016 in International Patent Application No. PCT/CA2016/050235 (8 pages).
(Continued)

*Primary Examiner* — Nicholas A Smith
(74) *Attorney, Agent, or Firm* — Ware, Fressola, Maguire & Barber LLP

(57) ABSTRACT

Disclosed herein is a system and method for sulphur-assisted carbon capture and utilization. The system includes a sulphur depolarized electrolyser (SDE) for receiving electricity, $H_2O$ and $SO_2$ and for electrolysing the $H_2O$ and $SO_2$ to produce hydrogen and sulphuric acid ($H_2SO_4$), a decomposition reactor for receiving and decomposing the $H_2SO_4$ into $SO_3$ and $H_2O$, wherein the $H_2O$ is recycled to the SDE, a sulphur submerged combustor for converting the $SO_3$ to $SO_2$ and producing $S_n$ vapor, a sulphur power plant for combusting $S_n$ vapor to produce $SO_2$, electricity and heat and for supplying the $SO_2$ and the electricity to the SDE and for supplying the heat to the decomposition reactor. The hydrogen is delivered to a carbon capture and utilization facility. An optional Flue Gas Desulphurisation (FGD) regenerable system removes $SO_2$ from flue gas, a $CO_2$ converter generates COS, and a separator separates the COS from the flue gas.

20 Claims, 6 Drawing Sheets

(51) Int. Cl.
*C25B 9/08* (2006.01)
*B01D 53/62* (2006.01)
*B01D 53/86* (2006.01)
*C01C 1/04* (2006.01)
*C10G 2/00* (2006.01)
*C07C 1/12* (2006.01)
*C07C 29/151* (2006.01)
*C25B 1/04* (2006.01)

(52) U.S. Cl.
CPC .............. *C07C 1/12* (2013.01); *C07C 29/151* (2013.01); *C10G 2/50* (2013.01); *C25B 1/02* (2013.01); *C25B 1/04* (2013.01); *C25B 1/22* (2013.01); *C25B 9/08* (2013.01); *B01D 2251/508* (2013.01); *B01D 2258/0283* (2013.01)

(56) References Cited

U.S. PATENT DOCUMENTS

| | | |
|---|---|---|
| 3,416,893 A | 12/1968 | Parish et al. |
| 3,764,661 A | 10/1973 | Kanazawa et al. |
| 3,888,750 A | 6/1975 | Brecher et al. |
| 3,904,387 A | 9/1975 | Kertamus et al. |
| 4,078,045 A | 3/1978 | Nakayama et al. |
| 4,122,156 A | 10/1978 | Kittrell et al. |
| 4,244,794 A | 1/1981 | Hollabaugh et al. |
| 4,306,950 A * | 12/1981 | Lu ............................ C25B 1/22 204/291 |
| 4,671,946 A | 6/1987 | de Kraa et al. |
| 5,204,082 A | 4/1993 | Schendel |
| 7,052,670 B2 | 5/2006 | Labrana Valdivia et al. |
| 7,067,101 B2 | 6/2006 | Rameshni |
| 7,090,818 B2 | 8/2006 | Stauffer |
| 8,956,526 B2 * | 2/2015 | Gorensek ................ C25B 15/08 205/637 |
| 2009/0000956 A1 * | 1/2009 | Weidner .................... C25B 1/02 205/637 |
| 2009/0220405 A1 * | 9/2009 | Lackner .................... C01B 3/06 423/431 |
| 2013/0217938 A1 | 8/2013 | Waycuilis et al. |

FOREIGN PATENT DOCUMENTS

| | | |
|---|---|---|
| CA | 2864792 | 8/2013 |
| DE | 1222024 | 8/1966 |
| EP | 1956293 | 8/2008 |
| EP | 2042470 | 4/2009 |
| GB | 957102 | 5/1964 |
| GB | 1560524 | 2/1980 |
| JP | 27632/1972 | 10/1972 |
| WO | 2009039611 | 4/2009 |
| WO | 2014117243 | 8/2014 |

OTHER PUBLICATIONS

International Energy Agency, "Annual Review 2013", Jul. 2014.
Luo Dongshen, Abatement of Pollution in Process of Synthesizing Carbon Oxysulfide by Using a New Catalyst, Qinghai Provincial Institute of Environmental Science, Xin ing, 1989.
Clark et al., "Mechanisms of CO and COS Formation in the Claus Furnace", 40 Ind. Eng. Chem. Res., 497-508, Dec. 21, 2000.
G. Mink, "Steady State Activity of Acidic, Basic and Amphoteric Oxide in the $CO_2+CS_2=2COS$ Reaction," 68 React. Kinet. Catal. Lett., 221-227, 1999.
U.S. Enviornmental Protection Agency, "Framework for Assessing Biogenic CO2 Emissions from Stationary Sources", Nov. 2014.
Agostini et al., "Carbon Accounting of Forest Bioenergy" JRC Scientific and Policy Reports, 2014.

* cited by examiner

SULPHUR-ASSISTED CARBON CAPTURE AND UTILIZATION (CCU) METHODS AND SYSTEMS

CROSS-REFERENCE TO RELATED APPLICATIONS

This application claims priority to International Application No. PCT/CA2016/050235, filed Mar. 4, 2016, which is hereby incorporated by reference in its entirety.

TECHNICAL FIELD

This invention generally relates to carbon capture and utilization (CCU) and, more particularly, to methods and systems for the sustainable production of hydrogen and electricity for the purpose of carbon capture and utilization (CCU).

BACKGROUND

The unrelenting rise in coal use without deployment of carbon capture and storage (CCS) is fundamentally incompatible with climate change objectives. The world faces an unabated global demand for energy, both for livelihood and for pure economic growth, as well as an existing, sizeable, carbon-intense infrastructure. There is no rational near-term energy future that does not involve continued use of fossil fuel. Maintaining coal-fired power generation would make practical sense if control of carbon dioxide ($CO_2$) could be made affordable. Current CCS technologies will not only increase capital costs but also impose significant performance penalties, challenging the competitiveness of coal power generation. Furthermore, many locations worldwide lack suitable geology for $CO_2$ storage, one of several factors expected to constrain CCS deployment.

Applicant attempted to solve this predicament as disclosed in patent applications entitled "Sulphur-assisted Carbon Capture and Storage (CCS) Processes and Systems" published as WO2014/117243, and also published as EP 2 950 911; CA 2,898,519; and US 2015/362188, and referred herein as a Hybrid Energy System or HES, in which $CO_2$ is recirculated by way of conversion to an intermediate sulphur compound, that is carbonyl sulphide (COS). The conversion enables utilization of the enormous latent chemical combustion energy value of sulphur (S) to generate complementary electric energy for the various energy-consuming steps in the CCS processes.

Carbonyl sulphide when reacted with sulphur dioxide ($SO_2$) reduces it back to sulphur and $CO_2$. Thus, the sulphur as a fuel feedstock is recycled, producing neither any detrimental environmental impact of sulphur oxides nor any solid waste. Application of this concept for power generation is virtually universal and a wide variety of arrangements or modifications to the proposed system are possible.

Sulphur Assisted CCS Capabilities and Shortcomings

The recirculation of carbon, which constitutes an underlying concept of carbon capture and utilization (CCU), aims to improve the economic viability of carbon capture. This may well result in accelerating intermediary measures to drive CCS deployment. However, CCU can contribute to alleviating global $CO_2$ emissions only if the recirculated $CO_2$ has come from power plants or industry—not from natural geologic sources as is common with, for example, conventional enhanced oil recovery (EOR). In addition, the energy required by the carbon capture and utilization process should come from carbon neutral sources.

In the cited disclosure, the specific prerequisite for the utilization of sulphur as a fuel is that the $CO_2$ already captured from power plants and/or industrial facilities be converted to an intermediate sulphur compound by an industrially proven process of catalytic oxygen/sulphur (O/S) exchange reaction with a common industrial solvent carbon disulphide ($CS_2$). However, the necessity of adding the $CO_2$ conversion system to the post-combustion $CO_2$ capture system increases complexity and raises the capital and operating costs of the power plant.

Moreover, to convert substantial quantities of carbon dioxide cost-effectively requires massive scale $CS_2$ manufacture. Fortunately, carbon disulfide can be synthesized from plentiful waste materials that are found around chemical, petroleum and other industries. As an example, in the Canadian oil sands, carbon disulphide can be rapidly and satisfactorily produced by the utilization of massive generated waste such as petroleum coke and large stockpiles of sulphur by using methods disclosed in various patent literature. Also, it can be alternatively formed by utilization of $H_2S$ from a gas stream containing lower molecular weight alkanes derived in the processing of tar sands (see, e.g., patent applications CA 2,864,792, and US 2013217938). However, the drawback of employing the carbon disulphide for the $CO_2$ conversion is that the carbon from $CS_2$ substantially increases the quantities of $CO_2$ equal to the volume being converted.

To avoid increasing the volume of $CO_2$, the conversion can be performed by the catalytic reaction of $CO_2$ with hydrogen sulphide ($H_2S$). This reaction is known in the art, and may be carried out in any suitable way known in the art. Typically, the reaction will be carried out by contacting gaseous carbon dioxide and gaseous hydrogen sulphide with a catalyst, in the presence of a sorbent. This specific method of $CO_2$ conversion to COS was commercially employed by Shell (see U.S. Pat. No. 4,671,946) at the North Sea Gas Terminal Emden, Germany as a conditioning method prior to distribution of the natural gas contaminated with a lean volume of $H_2S$. However, a more efficient catalyst system must be developed before this method can be applied for the purpose of $CO_2$ conversion.

Even so, with the substantial increase in quantities of $CO_2$ the HES can contribute to alleviating global $CO_2$ emissions and create value as depicted in FIG. 1, when the particular volume of the $CO_2$ captured from the power plant is converted to methanol, and the $CO_2$ from $CS_2$ is sequestrated. The supplemental electric energy can provide power for the electrolysis of water to produce the required hydrogen and to pressurize the $CO_2$ for transportation and storage. The ability to utilize the oxygen from the electrolysis for sulphur combustion can significantly improve the economic viability of HES. It is important to note here that electrolysis is one of the most efficient ways to get hydrogen from any form of water, whereby electricity can be converted into hydrogen with more than 80% efficiency.

Moreover, the methanation reaction is exothermic, and therefore a surplus of heat is generated in the process which can be utilized for the carbon capture process. In the case of carbon capture by chemical absorption with amine-based solution, the main energy demand arises from the regeneration of the rich solutions, which is achieved by the heating of the scrubbing liquids. It can be also used for the heating of water for the electrolysis, which will decrease the electricity requirement.

Another example of HES application is to provide energy for cryogenic oxygen generation. This implementation offers the possibility of rapidly retrofitting existing coal power plants to oxyfuel systems with the lowest costs compared to other zero emission technologies. The urgency of CCS retrofitting is further exacerbated by the significant lifetime of existing power plants and the very large number of plants likely to be built over the coming decades worldwide without $CO_2$ emissions abatement.

Then again, the preferred techniques for capturing $CO_2$ in cement plants are oxyfuel and post-combustion capture. However, $CO_2$ capture by oxyfuel technology will increase the cement production cost by around 40% (excluding $CO_2$ transport and storage costs) and post combustion liquid solvent scrubbing will increase the cost by around 70-100% (Annual Review 2013, www.ieaghg.org.). The same review concluded that post-combustion $CO_2$ capture (i.e. capture of $CO_2$ from different flue gases of the different combustion processes) in an integrated steel mill could be cost prohibitive for the reasons that it significantly increases the energy demand of the steel mill. The leading use of Oxy-Blast Furnace (OBF) Technology is one of the technology options considered to provide a significant reduction of $CO_2$ emissions from iron and steel production based on a blast furnace (BF) and basic oxygen furnace (BOF) route. In both of the above presented cases, the implementation of the HES as an energy provider can be the key for viable CCS for these industries.

Furthermore, one of the most significant enhancements of CCS by $CO_2$ conversion is that the COS compound introduces a flexibility that permits a much simpler, more energy-efficient means of $CO_2$ transportation when compared to a method in a supercritical phase. For example, the intermediate COS at 10° C. and 9 bar is a liquid with a density of 1 gm/cc and contains 0.2 gm carbon per cc, while at the same temperature and pressure $CO_2$ would be a vapour with a density of 0.018 gm/cc or 0.005 gm carbon per cc.

Thus, as depicted in FIG. 1, the $CO_2$ conversion plant or/and sulphur-fueled power plant can be foreseen as a hub for a CCS cluster of carbon-emitting facilities (e.g. steel, cement, lime, chemical industry, refining, and coal power plants) while simultaneously utilizing HES for addressing the hub participants' various energy-consuming steps in the CCS process. The ability to share a transport and storage network infrastructure is a major component of CCS cost reduction.

Moreover, the HES could be located either onshore and/or on vessels conveying the $CO_2$ or COS to offshore storage as depicted in FIG. 2. Ships offer flexibility in the $CO_2$ chain unlike pipelines. Transport by ship can provide flexibility in combining $CO_2$ from several sources, in changing capture sites, storage sites and the transportation routes in a CCS project, an attractive and viable alternative to overcome the limitations imposed by a "sink-source matching condition."

While pipelines require large capital expenditures up front, this is not the case with ships. Ships, on the other hand, have higher operating costs. The largest shipping cost components are electricity and fuel, each accounting for almost 30% of the total cost. Capital costs only contribute around 28% of the total shipping cost, compared to more than 70% for pipeline transport. By employing the HES for powering ship engines (steam/gas turbine), the logistics of transporting $CO_2$ to offshore storage areas will become economically feasible.

Hydrogen and Renewable Energy Sources Issues

The largest potential for the utilization of considerable quantities of $CO_2$ is in the process of making hydrocarbons that requires a supply on a massive scale of hydrogen. How to obtain the hydrogen still remains as an enduring challenge. The main obstacle for abundant production of $H_2$ by electrolysis is the high cost of electricity compared to petrochemical methods such as steam reforming of methane (natural gas), a source that is cheap but hardly green. The high cost of hydrogen production using electrolysis led to the search for a less expensive technology, one of which is the thermochemical cycle.

Thermochemical cycles are processes in which water is decomposed into hydrogen and oxygen via chemical reactions using intermediate elements which are recycled. The leading thermochemical processes that all have common high temperature reaction of thermal decomposition of sulphuric acid are three sulphur water-splitting cycles: Sulfur-Iodine (SI) process, Hybrid Sulfur (HyS) or Westinghouse process, and Ca—Br process (ANL modification of UT-3 cycle). The water-splitting cycles consist of a series of linked chemical reactions which result in the dissociation of water molecules into hydrogen and oxygen. All of the intermediate chemicals are regenerated and the only consumable is water.

Among these, the two-step Hybrid Sulfur (HyS) cycle presented schematically in FIG. 4 is one of the simplest, all-fluid thermochemical cycles that have been demonstrated at a laboratory scale to confirm performance characteristics. It was patented by Brecher and Wuin U.S. Pat. No. 3,888,750 in 1975 and extensively developed by Westinghouse in the late 1970s and early 1980s.

The key component of the HyS process is the electrolyser, also called a $SO_2$-depolarized electrolyser (SDE) where hydrogen ($H_2$) and sulphuric acid ($H_2SO_4$) are produced as products of the reaction between water and dissolved $SO_2$:

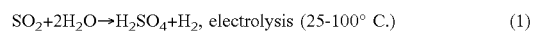

$$SO_2 + 2H_2O \rightarrow H_2SO_4 + H_2, \text{ electrolysis (25-100° C.)} \qquad (1)$$

The sulphuric acid is then decomposed at high temperature into sulphur dioxide, oxygen ($O_2$) and water ($H_2O$):

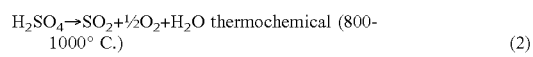

$$H_2SO_4 \rightarrow SO_2 + \tfrac{1}{2}O_2 + H_2O \text{ thermochemical (800-1000° C.)} \qquad (2)$$

The presence of sulphur dioxide along with water in the electrolysis reduces the required electrode potential to well below that required for electrolysis of pure-water, thus reducing the total energy consumed by the electrolysis. In practice, $SO_2$ electrolysis may require no more than 25% of the electricity needed in the alkaline water electrolysis, although at the expense of the need to decompose $H_2SO_4$ at high temperatures in order to recycle the $SO_2$.

The decomposition of $SO_3$ to $SO_2$ is thermodynamically unfavourable at lower temperatures, so it is carried out at temperatures above 800° C. in order to produce a sensible equilibrium conversion. To be feasible, the process was designed to be coupled with a very high temperature nuclear power plant, which would supply both the heat needed for the sulfuric acid concentration and decomposition steps and the electricity required for the electrochemical part. A very high temperature reactor belongs to the group of "Generation IV" nuclear power plants, which have yet to be constructed. Additionally, the cycle needs an expensive chemical plant.

The coupling of the HyS cycle with a solar heat source has also been studied in an attempt to achieve sufficiently high temperatures for sulfuric acid decomposition. Water electrolysis powered by renewable energy resources would produce only hydrogen and oxygen, avoiding the emission of $CO_2$; however, renewable energy resources alone are inadequate.

Producing electricity from direct solar radiation or wind is limited by the unpredictability and variability of these sources. Currently, wind power is the fastest growing renewable energy source, especially in Europe. For example, in Denmark, over 20% of the demand for electricity is generated by wind power. However, at an optimum location, generally offshore, a windmill-driven generator will only run at its nominal power during 30% of the time, while at most land-based locations wind generators typically operate at nominal power 20% of the time.

Compensating for the rapid fluctuations in output of large-scale wind and solar-based generators is difficult for the conventional steam-based power plants, lowers the utilisation factor of the other power plants, which increase the capital costs per kWh. Running conventional fuel-based power plants at a low load drastically increases their fuel consumption, increases their $CO_2$ emission, and drastically increases their maintenance costs per kWh.

Technologies which provide these capabilities are in place, e.g., gas engines, which are low in emissions, quick and flexible and also allow heat recovery and energy storage integration. Yet, with coal still being the cheapest fuel in most parts of the world, natural gas has a hard time to compete.

Furthermore, the CCS concept assumes that the station is running at a constant level of power generation and carbon emissions. As such, there is yet no method to alleviate the effect of changes in demand on the CCS.

Switching from fossil fuels to bioenergy does not necessarily reduce $CO_2$ emissions overall. Depending on how the biomass is produced and used, the resulting emissions and climate impact can be better or worse when compared to fossil fuels. The JRC, the European Commission's in-house science service, states that "the assumption of biogenic carbon neutrality is not valid under policy relevant time horizons" (Carbon accounting of forest bioenergy, 2013). In addition, the US Environmental Protection Agency recognises that "carbon neutrality cannot be assumed for all biomass energy a priori (Framework for Assessing Biogenic $CO_2$ Emissions from Stationary Sources, 2014).

The main environmental drawback of large-scale electricity generation from geothermal energy (specifically in volcanic areas such as Iceland) is that the wells contain high amounts of $COz_2$, derived from metamorphism of carbonate, which produce worldwide average emissions of 122 g $CO_2$ per generated $kWh_e$.

For a short- to medium-term application, a new alternative Outotec® open cycle process (OOC) has been proposed for hydrogen production. This process involves only one stage (SDE) and does not require sulfuric acid decomposition. The $SO_2$ used in the process can be obtained from flash smelting, sulfides roasting, sulfur combustion or any other similar operation, and because sulfuric acid is a commercial product, the cycle may be left open.

Although various systems and methods for carbon neutral energy and hydrogen production are disclosed in the prior art, all or almost all of them suffer from one or more disadvantages. Thus, there is still a need to provide methods and systems that provide an improvement over the prior art.

SUMMARY

In general, and by way of overview, the present invention relates to a novel sulphur-assisted system and related method for carbon capture and utilization. This system and method exploits a sulphur thermochemical water-splitting process to efficiently generate hydrogen. This sulphur thermochemical water-splitting process referred herein as a HTS is able to operate at significantly lower temperatures with reduced complexity by employing a sulphur depolarized electrolyser (SDE) that receives its thermal and electric power from a sulphur-combusting power plant.

More specifically, the system and method use the sulphur depolarized electrolyser (SDE) for receiving electricity, $H_2O$ and $SO_2$ and for electrolysing the $H_2O$ and $SO_2$ to produce hydrogen and sulphuric acid ($H_2SO_4$), a decomposition reactor for receiving and decomposing the $H_2SO_4$ into $SO_3$ and $H_2O$, wherein the $H_2O$ is recycled to the SDE. The system also includes a sulphur submerged combustor for converting the $SO_3$ to $SO_2$ and producing $S_n$ vapor. The system further includes a sulphur power plant for combusting $S_n$ vapor to produce $SO_2$, electricity and heat and for supplying the $SO_2$ and the electricity to the SDE and for supplying the heat to the decomposition reactor. The hydrogen is delivered to a carbon capture and utilization facility where it can be reacted with carbon dioxide to form fuels or chemicals.

In light of the foregoing, one inventive aspect of the present disclosure is a system for sulphur-assisted carbon capture and utilization. The system includes a a sulphur depolarized electrolyser (SDE) for receiving electricity, $H_2O$ and $SO_2$ and for electrolysing the $H_2O$ and $SO_2$ to produce hydrogen and sulphuric acid ($H_2SO_4$), a decomposition reactor for receiving and decomposing the $H_2SO_4$ into $SO_3$ and $H_2O$, wherein the $H_2O$ is recycled to the SDE. The system also includes a sulphur submerged combustor for converting the $SO_3$ to $SO_2$ and producing $S_n$ vapor. The system further includes a sulphur power plant for combusting $S_n$ vapor to produce $SO_2$, electricity and heat and for supplying the $SO_2$ and the electricity to the SDE and for supplying the heat to the decomposition reactor. The hydrogen is delivered to a carbon capture and utilization facility where it can be reacted with carbon dioxide to form fuels or chemicals.

Another inventive aspect of the present disclosure is a method of sulphur-assisted carbon capture and utilization. The method entails receiving electricity, $H_2O$ and $SO_2$ at a sulphur depolarized electrolyser (SDE), electrolysing the $H_2O$ and $SO_2$ to produce hydrogen and sulphuric acid ($H_2SO_4$), receiving and decomposing the $H_2SO_4$ into $SO_3$ and $H_2O$, recycling the $H_2O$ to the SDE, converting using a sulphur submerged combustor the $SO_3$ to $SO_2$ and producing $S_n$ vapor, combusting $S_n$ vapor to produce $SO_2$, electricity and heat, supplying the $SO_2$ and the electricity to the SDE, supplying the heat to the decomposition reactor and delivering the hydrogen to a carbon capture and utilization facility.

Other aspects and features of the invention will appear to those skilled in the art upon examination of the following description and the claims and drawings attached thereto.

BRIEF DESCRIPTION OF DRAWINGS

Further features and advantages of the present invention will become apparent from the following detailed description, taken in combination with the appended drawings, in which.

DETAILED DESCRIPTION OF EMBODIMENTS

Disclosed below are exemplary embodiments of systems and methods for the sustainable generation of electric energy and hydrogen.

Figure 3:
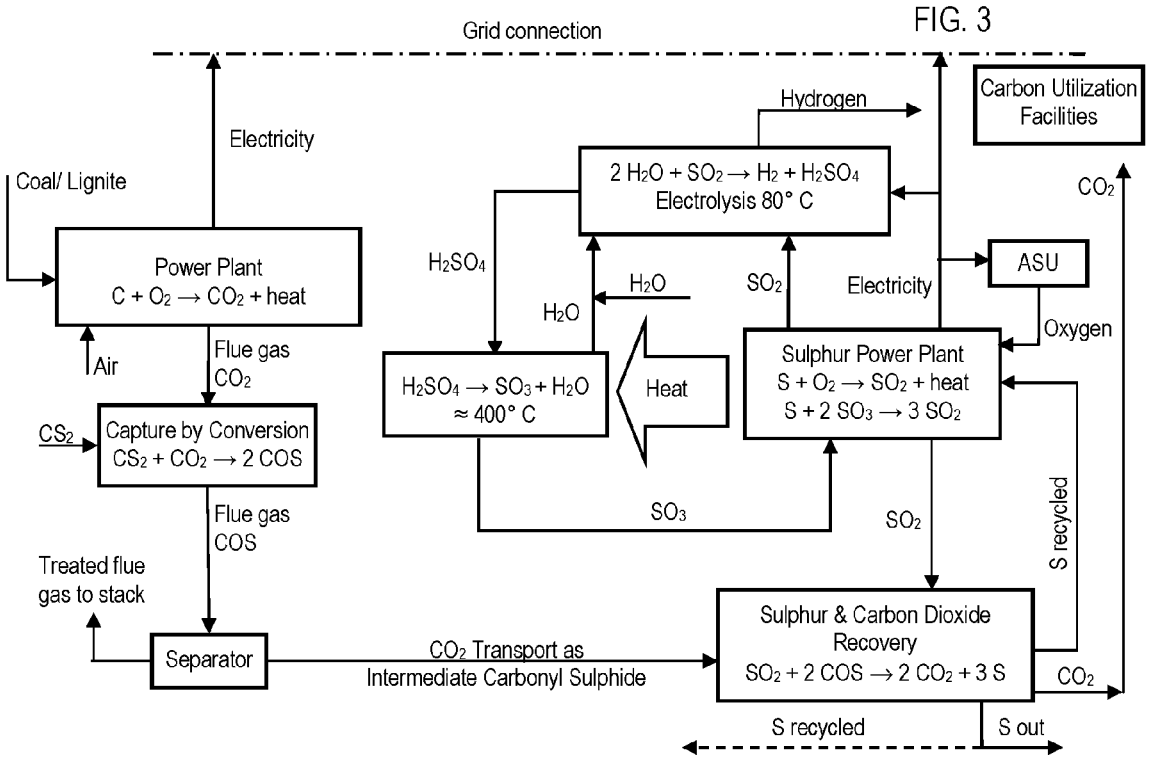
FIG. 3 is schematically presents an overview of a system in accordance with embodiments of the present invention.

By way of overview, FIG. 3 schematically presents a system that includes a converter for receiving a carbon disulphide and flue gas containing carbon dioxide to be captured from the flue gas by conversion to carbonyl sulphide, a separator for receiving a flue gas and carbonyl sulphide and separating the carbonyl sulphide from the flue gas, a sulphur and carbon dioxide recovery unit for receiving the carbonyl sulphide and sulphur dioxide, a sulphur-fueled power plant for combusting sulphur to generate sulphur dioxide and electric power, a hydrogen generation facility that uses the electric power to generate hydrogen that is supplied to a carbon utilization facility. The system may include a condenser (not show) for receiving and separating carbon dioxide and carbonyl sulphide and for delivering the carbon dioxide to the carbon utilization facility while returning the carbonyl sulphide to the sulphur and carbonyl sulphide recovery unit. The function and role of each of these components of the system will be further described below.

Figure 4:
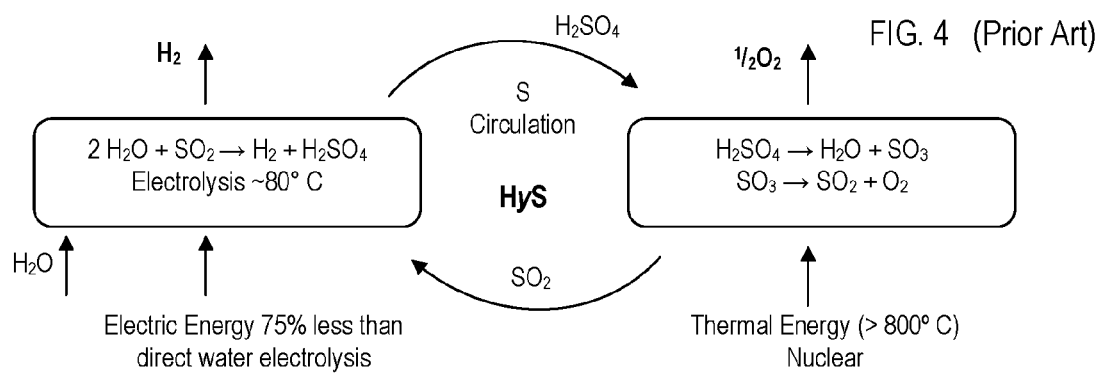
FIG. 4 is a schematic of a prior-art HyS process.
Figure 5:
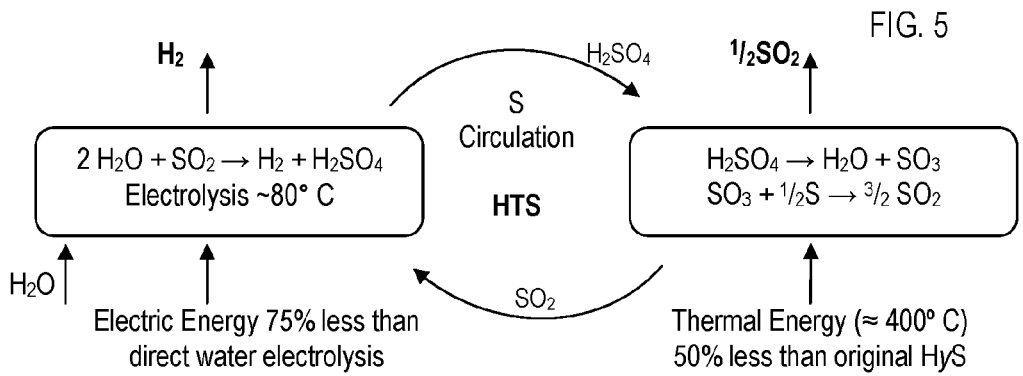
FIG. 5 is a conceptual schematic of a thermochemical $H_2$ process (HTS) used in embodiments of the present invention.

Also by way of overview, the hydrogen thermochemical sulphur process (HTS) depicted in FIG. 5 represents an improvement over the cycle disclosed in FIG. 4. This will also be elaborated below in greater detail.

Figure 6:
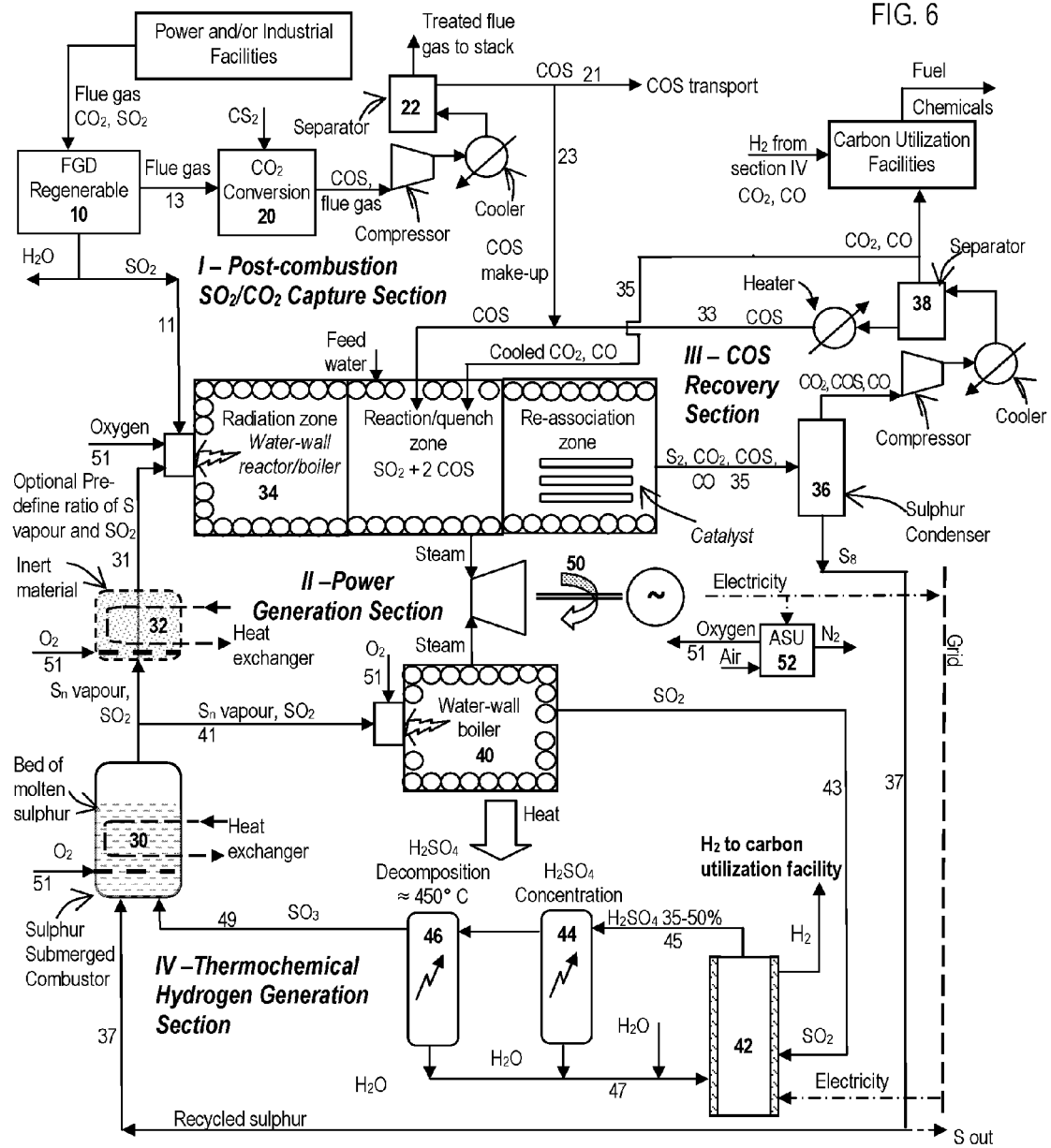
FIG. 6 is an exemplary embodiment of the system that is able to sustainably generate electric energy and hydrogen.

Referring now to FIG. 6, an exemplary embodiment of the system comprises a post-combustion $SO_2/CO_2$ capture system section I composed of a Flue Gas conversion unit, compressor, cooler and separator; a power generation section II made up of a sulphur-submerged combustion furnace 30, an optional sulphur vapour combustion chamber 32, a water-wall reactor/boiler 34, a sulphur condenser 36, a steam turbogenerator 38; and a COS recovery section III which separates the reactor gas products. The COS recovery section contains a compressor, cooler and separator. These three sections cooperate to constitute a system that is able to sustainably generate electric energy and hydrogen.

As presented in FIG. 6, flue gas from power and/or industrial facilities, after removal of particles (not shown), is first directed to the Flue Gas Desulphurisation (FGD) 10 preferably a Wellman-Lord FGD system, that has a capacity to produce concentrated $SO_2$ through using a regenerable sorbent and the possibility to combine $SO_2$ control with the control of other pollutants. The dry separated $SO_2$ from the FGD 10 acts as a dilutant and is directed by a conduit 11 to a water-wall reactor/boiler 34 and the desulphurized flue gas is directed by a conduit 13 to the $CO_2$ separation facility 20.

The current leading technique for separating carbon dioxide from post-combustion flue gas involves the use of a sorbent that will preferentially adsorb the carbon dioxide from the flue gas. Once the sorbent becomes saturated with carbon dioxide, it can be heated, which will cause the carbon dioxide to desorb at high purity. There are two possible adsorption mechanisms: physisorption, where the target molecules are attracted to the surface of pore walls within a high surface-area sorbent by van der Waals forces which leaves the chemical species of the adsorbate and surface intact, or chemisorption, where the target gas undergoes a covalent chemical reaction to bind to certain sites on the sorbent.

The problem with this approach is, in the case of amine-based post-combustion $CO_2$ capture, that about 70% of the energy is expended during solvent regeneration for $CO_2$ stripping. Therefore, the technique for separating carbon dioxide at system 20 from post-combustion flue gas of the embodiment of FIG. 6 entails the use of a heterogeneous catalysis for the conversion of the $CO_2$ to COS.

The chemisorbed $CO_2$ onto a surface of a solid catalyst forms strong bonds between adsorbate molecules and specific active sites of the catalyst surface which are sufficiently reactive to promote (catalyze) chemical reaction with gaseous or concurrently weakly chemisorbed carbon disulphide ($CS_2$) to produce carbonyl sulphide (COS) that desorbs as a product from the surface of the catalyst. The reaction can be catalyzed by metal oxides such as alumina (gamma-$Al_2O_3$); however, according to Mink, the highly ionic lanthana ($La_2O_3$) and thoria ($ThO_2$) exhibited peculiar acid-base properties and superior catalytic activity (G. Mink, Steady state activity of acidic, basic and amphoteric oxide in the $CO_2+CS_2=2COS$ reaction, *React. Kinet. CataL Lett.*, Vol. 68, No. 2, 221-227, 1999).

Figure 1:
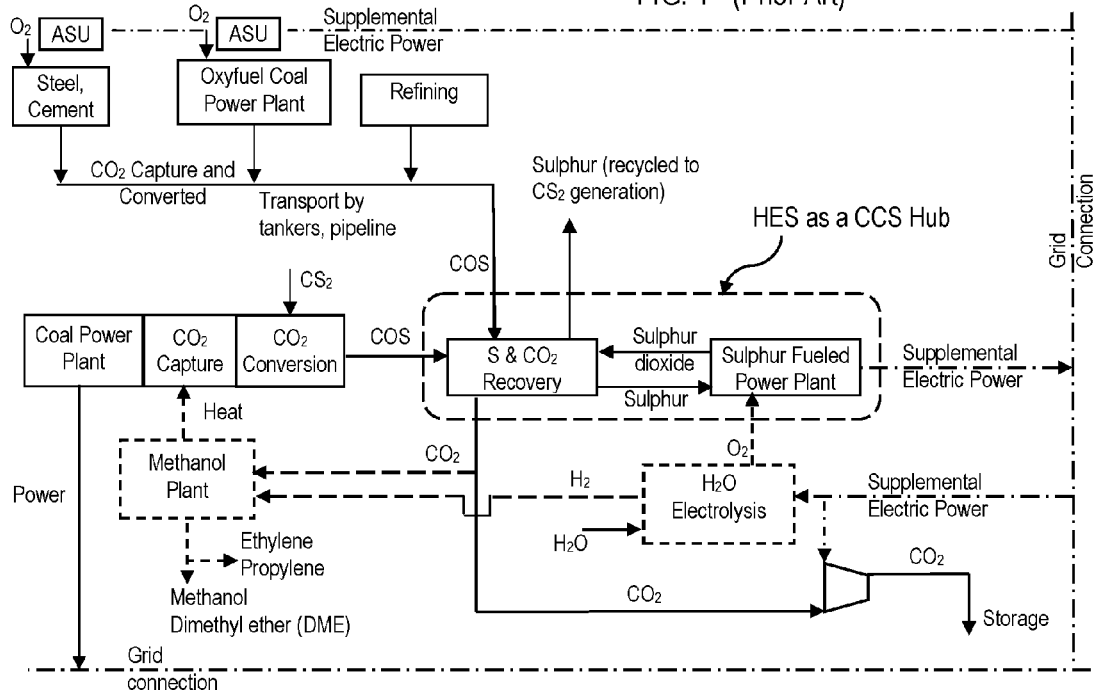
FIG. 1 is a schematic of an HES as a CCS hub in accordance with the prior art.
Figure 2:
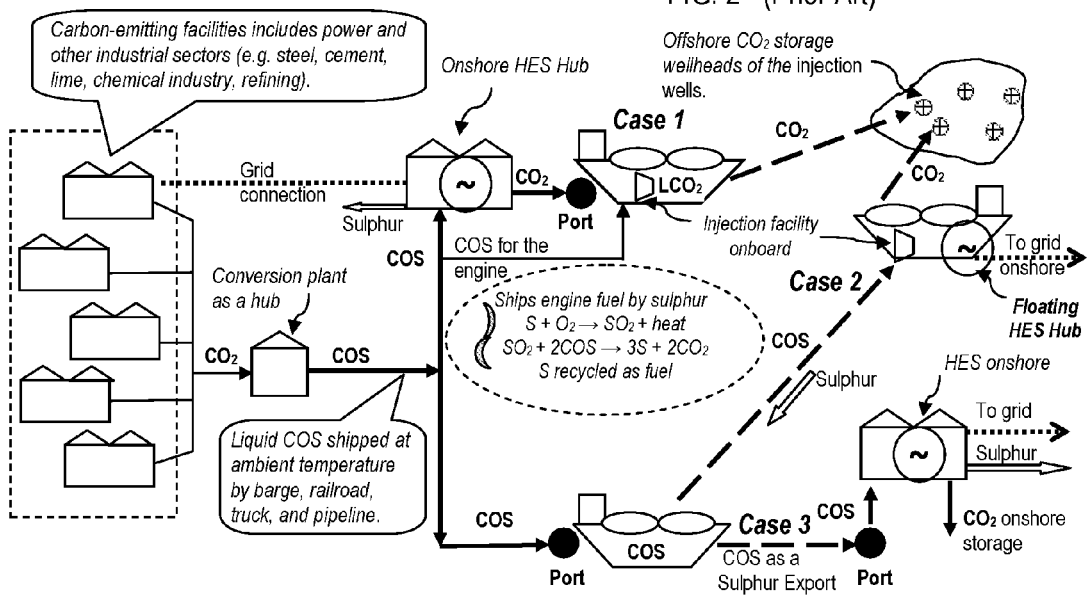
FIG. 2 is a schematic of a prior-art HES which may be flexibly located either onshore and/or on vessels conveying the $CO_2$ or COS to an offshore storage.

The uncondensed gases from conversion unit 20 composed primarily of carbon dioxide and carbonyl sulphide are introduced to a compressor operated at approximately 20 atm. The resulting compressed gases are subsequently transferred to a cooler where their temperature is reduced to about 0° C. The gas-liquid phase mixture produced in the cooler is withdrawn and transferred to a separator 22, where the carbonyl sulphide present in the product gases is removed therefrom through conduit 21 for the future handling as shown in FIG. 1 and/or FIG. 2 and through conduit 23 as a make-up to water wall boiler 34 for the reaction with $SO_2$.

In comparison with the cited previous disclosure the implication of doing so is that the use of amine-based post-combustion system is eliminated and thus the complexity of the capture system, capital and operating cost and size of the plant are all reduced.

Very high heat energy is produced by the combustion of sulphur vapour in pure oxygen. The gaseous sulphur fuel comprises a combination of various sulfur allotropies with sulphur dioxide as a diluent. The sulfur allotropies $S_n$ and $SO_2$ may be provided to the water-wall boiler by the submerged sulphur combustor 32.

Oxygen is sparged into a pool of molten sulphur at the appropriate temperature and immediately reacts to form sulphur dioxide. The heat of reaction causes the pool of sulphur to boil, but the temperature of the system is limited to the boiling point of sulphur at the operating pressure of the reactor. The amount of sulphur vaporised is such that the heat of vaporisation is exactly equal to the heat of reaction. Even at atmospheric pressure, the boiling point of sulphur (444.6° C.), is well above the auto ignition temperature (auto ignition of sulphur in air is 243° C.). This ensures immediate and complete reaction of the oxygen with sulphur as it enters the reactor. Accordingly, because oxygen is always the deficient reactant, there is no possibility of forming sulphur trioxide. Even if some transient $SO_3$ is created, it would immediately react with the excess sulphur to form sulphur dioxide. Exemplary submerged sulphur combustors and related process are disclosed in U.K. Patent No. 1,560,524 and U.S. Pat. No. 5,204,082.

To overcome the temperature and pressure limitations associated with refractory linings, the water-wall boiler 34 is employed. The water-wall boiler is an advanced technology that is well proven, well known, established, and deployed at a very large scale in current industrial applications. The design of the water-wall boiler/reactor 34 is based on the modified Claus process WorleyParsons water-wall boiler capable of withstanding a bulk gas temperature of up to 2760° C. and disclosed in U.S. Pat. No. 7,067,101. The water-wall boiler may produce saturated and/or superheated steam utilized by the steam turbine 38 for the power generation.

The water-wall boiler 34 has a radiant section, using water-wall tubes, capable of withstanding a very high gas temperature. In addition, the flame temperature can be controlled by different $O_2$, S and $SO_2$ mass ratios that can be pre-defined by the submerged combustion process parameters, such as pressure, temperature, and heat loss. Additionally, the composition of the mixture can be regulated by withdrawing part of the heat using special heat-exchangers located in the bubbling bed. Optionally, it also can be regulated by an enclosed additional chamber 32 loaded with inert material having high heat transfer coefficients in which the vapour-gas mixture, as it issues from the bubbling chamber 30, can react with the secondary oxygen delivery through conduit 19 for the further partial combustion of the sulphur vapour. The temperature of the combustion for the different $O_2$, S and $SO_2$ mass ratios can be provided through HSC reaction simulated program such as the one developed by Outokumpu as disclosed in U.S. Pat. No. 7,052,670.

A sufficient furnace volume is provided in the reaction/quench zone to achieve a desired level of completion of the $SO_2$ and COS reaction. The products of the high-temperature homogeneous gas-phase reaction between COS and $SO_2$ do not merely yield sulfur and $CO_2$ but a significant amount of CO as well. In a non-stoichiometric operation, the excess reactant (COS or $SO_2$) will also be present (Clark et al, *Ind. Eng. Chem. Res.*, 2001, 40 (2), 497-508).

Equally, to give insight into how fast the reaction between COS and $SO_2$ can occur and how the various reaction products evolve as a function of reaction time, Applicant in a disclosure entitled "Methods and systems for sulphur combustion" published as CA 2,700,746, EP2203680, provided kinetic results of the simulation in COMSOL Reaction Engineering Laboratory software using the Leeds Sulphur Mechanism Version 5.2. The reaction conditions chosen for $COS:SO_2$ feed ratios of 0.5:1, 1:1, and 2:1 respectively at a temperature of 1625 K (1351.85° C.) and pressure of 10 atm. The time axis has units of seconds.

The reaction is extremely rapid and the most significant species of the reaction are $CO_2$, $S_2$ and CO. The kinetic simulations also show that the reaction product distribution expectedly varies with time. However, an important insight gained from the simulation results is that, at a very early stage (<<100 ms), the primary product of the reaction is CO and $S_2$ but, at longer times, the formation of $CO_2$ occurs seemingly at the cost of CO consumption. The implication of this insight is that that the reaction product composition can, in principle, comprise primarily CO and $S_2$ by controlling reaction times of interaction of these gases by rapid quenching.

Gases have a low heat capacity and thus such reaction conditions can be realized, and the resulting reaction product would be favorable thermodynamically at low temperatures for re-association of CO and sulphur to yield COS in the lower temperature re-association zone of the water-wall boiler 34 which contains a bed or series of beds of suitable catalyst.

There are several catalysts described in the patent literature for the process of producing carbonyl sulfide by reacting carbon monoxide with sulfur. West German Patent No. 1,222,024 discloses a technique to react carbon oxide with sulfur at relatively high temperature of 350° to 510° C., and U.S. Pat. No. 2,983,580 discloses the reaction of carbon monoxide at relatively low temperature of 260° to 483° C. in the presence of an aluminosilicate having a three dimensional structure. Similarly, U.S. Pat. No. 3,416,893 and U.K. Patent No. 957,102 discloses techniques to react carbon monoxide with sulfur in the presence of a sulfide having a metal selected from the group consisting of metals in the V, VI, VII and VIII groups of the periodic table, and Japanese Patent Publication No. 27632/1972 and U.S. Pat. No. 3,764,661 disclose techniques to react in the presence of an alkali metal sulfide such as sodium and potassium sulfides. Also, U.S. Pat. No. 4,078,045 discloses a technique for producing carbonate sulfide by reacting carbon monoxide with sulfur in the presence of an alkaline earth metal compound selected from the group consisting of calcium, strontium or barium sulfides sulfates and halides.

However, an extensive scientific literature search showed that the highly reactive and selective ferrous disulfide ($FeS_2$) is the optimum catalyst for COS synthesis at a temperature of 360-450° C. During the seven years following its commercialization in 1981, the catalyst delivered consistently superb performance (Luo Dongshen, Abatement of Pollution in Process of Synthesizing Carbon Oxysulfide by Using a New Catalyst, Qinghai Provincial Institute of Environmental Science, Xin ing, 1989).

The resulting gaseous reaction products from a re-association zone of the water-wall boiler 34 are sent next through conduit 35 to condenser 36 where they are cooled to a temperature of about 150° C. to separate liquid sulphur via conduit 37. The uncondensed gases composed primarily of carbon dioxide, carbonyl sulphide together with a small amount of carbon monoxide are introduced to the compressor being operated at approximately 20 atm. The resulting compressed gases are next transferred to the cooler where their temperature is reduced to about 0° C. The gas-liquid phase mixture produced in the cooler is withdrawn and transferred to the separator 38, where the carbonyl sulphide present in the product gases is removed therefrom through conduit 33, heated and directed as a gas to the reaction zone of the water-wall boiler 34.

Under the temperature condition employed in the re-association zone of the water-wall boiler 34 only a small amount of carbon monoxide remains unconverted. Accordingly, under such circumstances it will generally be found uneconomical to separate the carbon dioxide from the gases by amine absorption or other such method merely for the purpose of recycling the comparatively small amount of unconverted carbon monoxide to the reaction/quench zone of the boiler-reactor 34. However, it may warrant the recycling of the gaseous mixture of $CO_2$/CO effluent from the separator 38 through conduit 35 to the reaction/quench zone of the water-wall boiler 34 for the rapid quenching of the $SO_2$/COS reaction gas products. It should be especially appreciated that the $CO_2$/CO gas mixture from the separator 38 is already cooled to a temperature of about 0° C.

Referring still to FIG. 6, a thermochemical $H_2$ generation section IV includes an evaporating reactor 44 for evaporating/concentrating sulphuric acid ($H_2SO_4$) and a decomposing reactor 46 for decomposing the sulphuric acid ($H_2SO_4$). The thermochemical $H_2$ generation section IV also includes an electrolyser, more specifically a sulphur depolarized electrolyser (SDE) 42, for the electrolysis of a mixture of sulfur dioxide and water. The thermochemical $H_2$ generation section IV also includes the water-wall boiler 40. Additionally, there is a sulphur condenser (not shown) that may be required for removing any trace of sulphur from the $SO_2$ gas.

The thermochemical $H_2$ generation process is performed according to the following reactions (1) (3) and is presented schematically in FIG. 5:

$$SO_2+2H_2O \rightarrow H_2SO_4+H_2, \text{ electrolysis (25-100° C.)} \quad (1)$$

$$H_2SO_4 \rightarrow H_2SO_4 \rightarrow SO_3+H_2O \quad T=350\text{-}450° C. \quad (3)$$

The embodiment depicted in FIG. 6 reveals the distinctiveness of the thermochemical $H_2$ generation process (HTS) by means of providing the required thermal energy and electricity itself. Besides that, all sulphur is recycled owing to integration with HES. Advantageously, the sulphur trioxide ($SO_3$) is directly used from the $H_2SO_4$ decomposition reactor 46 as an oxygen carrier to the bed of molten sulphur of the submerged combustor 30 where the $SO_3$ undergoes chemical reduction by the exothermic reaction (4):

$$2SO_3+S \rightarrow 3SO_2+\text{heat } \Delta H=-99 \text{ kJ/mol} \quad (4)$$

Figure 7:
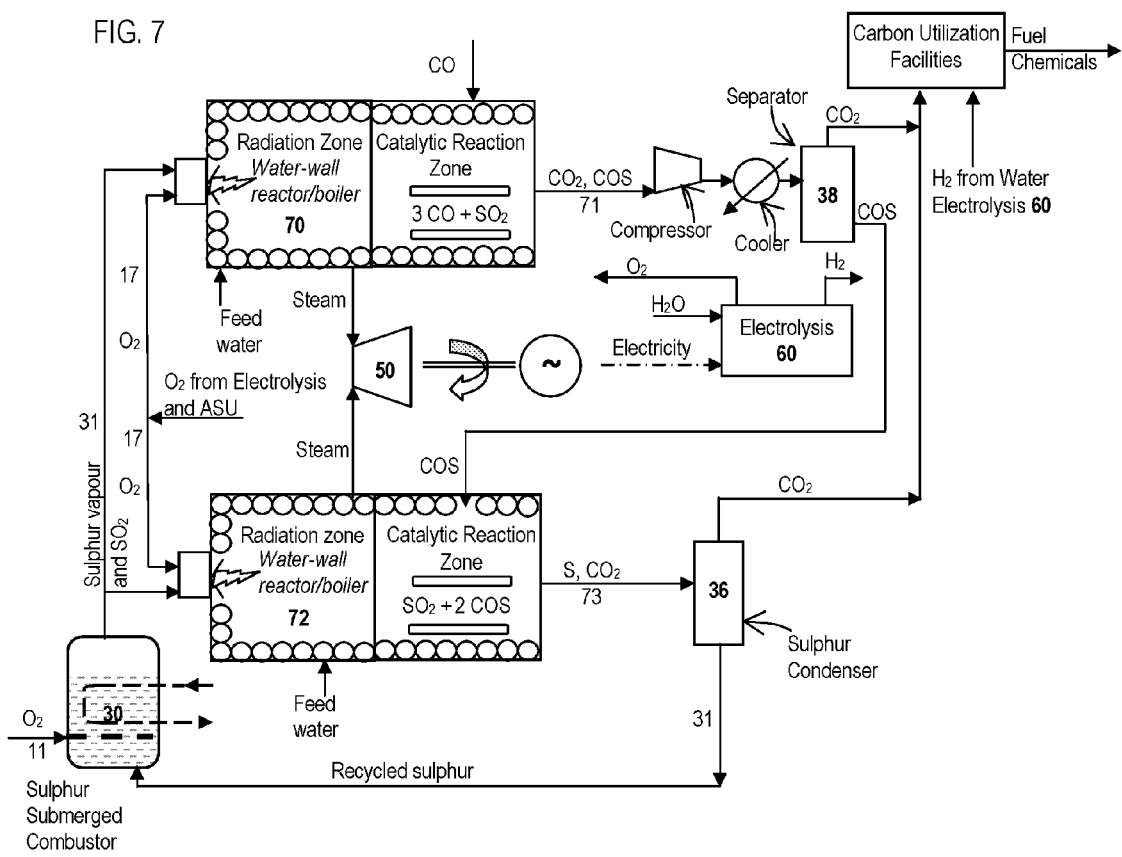
FIG. 7 is an exemplary embodiment of the "stay alone" sulphur-fueled power plant as a system to provide sustainable energy for the order of the processes for $CO_2$ utilization.

As depicted in FIG. 7, a "stay alone" sulphur-fueled power plant is part of an exemplary embodiment of a system that provides sustainable energy for the processes of $CO_2$ utilization. The embodiment depicted in FIG. 7 includes two water-wall boilers, namely a first water-wall boiler 70 in which the catalytic reaction zone contains a bed or series of beds of suitable catalyst to convert the $SO_2$ to COS, and a second water-wall boiler 72 in which the catalytic reaction zone contains a bed or series of beds of suitable catalyst to reduce the $SO_2$ to sulphur and carbon dioxide.

The catalytic conversion of the $SO_2$ to COS is well known in the literature as exemplified by U.S. Pat. No. 4,122,156. This reaction is promoted by a catalyst of the type containing a reducible metal oxide. Chromium promoted iron catalyst has been found to be effective in this application. Other metal promoted catalysts, however, may be used, including nickel-molybdenum, cobalt-molybdenum, molybdenum or any suitable combination thereof. The thermodynamics for this reaction are extremely favorable. As an approximation, the reaction can be carried out in the range of 200° to 500° C. Also of interest is the fact that the reaction is highly exothermic. A substantial quantity of heat must be removed from the reaction in order to control the temperature.

The reduction of $SO_2$ by reacting with COS in the catalytic reaction zone of the second boiler 72 produces S and $CO_2$ for delivery through conduit 73 to the sulphur condenser 36. As shown in FIG. 7, the sulphur condenser 36 separates S from $CO_2$. The sulphur (S) is recycled to the sulphur submerged combustor whereas the $CO_2$ is piped or transported to carbon utilization facilities.

As shown in FIG. 7, $O_2$ is supplied to the sulphur submerged combustor to react with the recycled sulphur (S) to produce sulphur vapour and $SO_2$ which are supplied via conduit 31 to the first and second water-wall reactors/boilers 70, 72. Oxygen ($O_2$) from electrolysis and an air separation unit (ASU) is delivered via conduit 17 to the first and second water-wall reactors/boilers 70, 72. Each of the water-wall reactors/boilers 70, 72 includes a radiation zone and a catalytic reaction zone. The radiation zone of the first water-wall boiler 70 receives feed water. The catalytic reaction zone of the first water-wall boiler 70 receives carbon monoxide. The radiation zone of the second water-wall boiler 72 receives feed water. The catalytic reaction zone of the second water-wall boiler 72 receives COS. The first and second water-wall boilers 70, 72 generate steam to drive a steam turbine generator 50 that generates electricity to power an electrolyser (electrolysis unit) 60 which also receives water. The electrolyser 60 splits the water molecules to thereby produce $H_2$ and $O_2$, the oxygen being optionally recycled in whole or in part to the sulphur submerged combustor.

As further depicted in FIG. 7, the first boiler 70 generates $CO_2$ and COS which are supplied via conduit 71 to a compressor followed downstream by a cooler and a separator 38 which separates the COS from the $CO_2$. The COS is recycled to the second water-wall boiler 72, specifically to the catalytic reaction zone thereof. The $CO_2$ is delivered to the carbon utilization facilities as shown in the figure. The $H_2$ generated by water electrolysis may be fed to the carbon utilization facilities to produce fuels (e.g. hydrocarbons) and/or chemicals.

The basic process for converting solid coal to fuel gas in the form of carbon monoxide is well known. In fact, the "town gas," used before the availability of natural gas, was produced by burning coal under a reducing atmosphere. Present day coal gasification processes involve the combustion of char or coke with oxygen to yield a combustible gas through the following reaction:

$$C+\tfrac{1}{2}O_2 \rightarrow CO$$

Where the process uses oxygen instead of air, such extreme temperatures are generated that some steam addition is necessary to moderate the gasification temperature. With steam addition, a second consuming reaction occurs to reduce heat liberation and produce hydrogen and carbon monoxide.

Kertamus et al., U.S. Pat. No. 3,904,387, discloses a combustible fuel gas that is produced by heating solid char or coke whereby sulfur dioxide is used for the gasification stage and is enriched with oxygen. The process produces gaseous carbon monoxide and elemental sulphur.

It is important to note that the above described method of COS production can be used to produce carbon disulphide as disclosed in U.S. Pat. No. 7,090,818.

Figure 8:
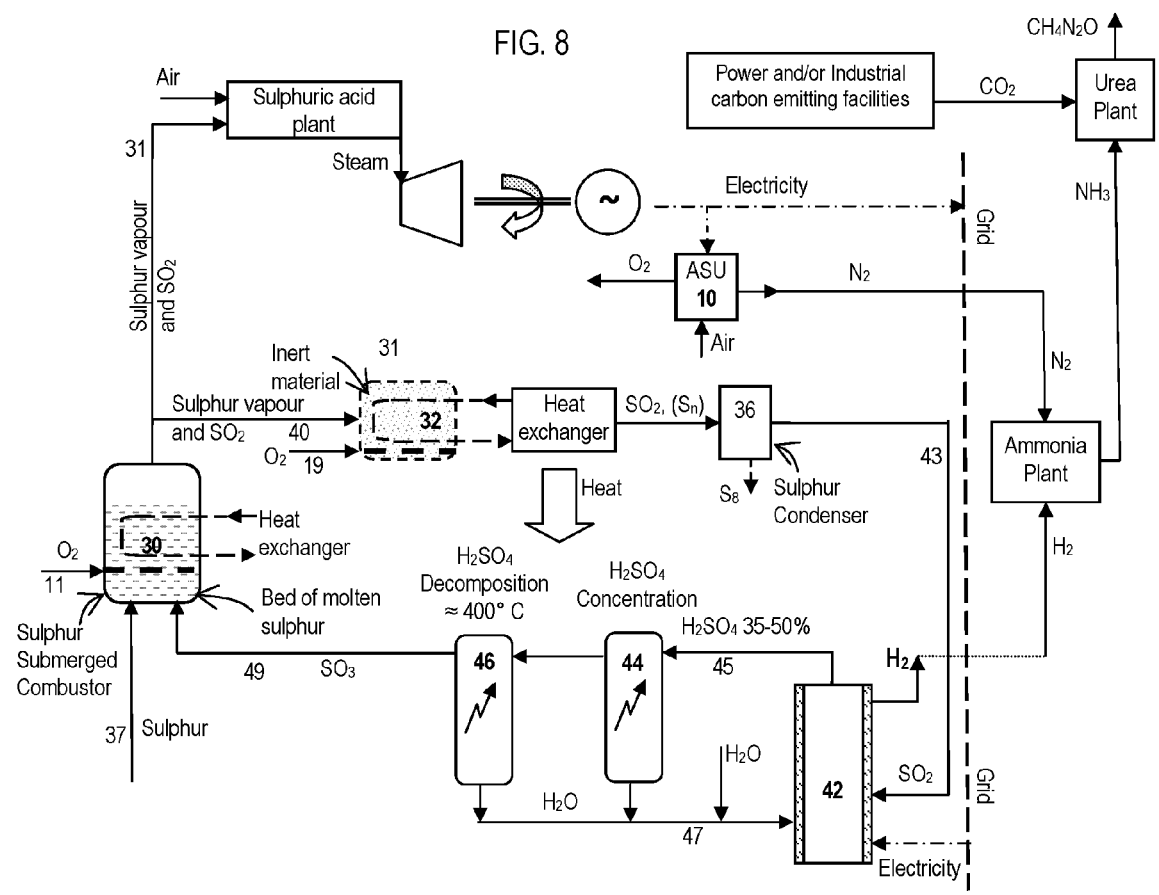
FIG. 8 is an exemplary embodiment of the hydrogen thermochemical sulphur cycle incorporated with a conventional sulphuric acid plant for the concurrent sustainable production of hydrogen, ammonia and utilization of carbon dioxide for the production of urea.

FIG. 8 illustrates an exemplary embodiment of a hydrogen thermochemical sulphur process (HTS) cooperating with a conventional sulphuric acid plant which does not require any undue modification for integration with the hydrogen thermochemical sulphur cycle. As illustrated in FIG. 8, the sulphuric acid plant receives air as well as sulphur vapour and $SO_2$. The sulphur and $SO_2$ are supplied via conduit 31 from a sulphur submerged combustor that is fed with oxygen ($O_2$) via conduit 11 and elemental sulphur via conduit 37. The sulphur submerged combustor is also fed with $SO_3$ via conduit 49. The $SO_3$ derives from an evaporating reactor 44 and a decomposing reactor 46 which respectively evaporate and decompose the sulphuric acid ($H_2SO_4$) generated by the sulphur depolarized electrolyser (SDE) 42. As illustrated in FIG. 8, the sulphur depolarized electrolyser (SDE) 42 receives electricity (e.g. from the power grid), $SO_2$ from a sulphur condenser 36 and a supply of water via conduit 47 which are produced by the evaporating reactor 44 and the decomposing reactor 46.

As depicted in FIG. 8, the hydrogen ($H_2$) produced by the sulphur depolarized electrolyser (SDE) 42 is provided to an ammonia plant. The ammonia plant also receives nitrogen ($N_2$) to produce $NH_3$ which is then delivered to a urea plant.

The urea plant receives carbon dioxide from a power plant or other industrial carbon-emitting facility. The urea plant uses the carbon dioxide and delivers the $NH_3$ to produce $CH_4N_2O$.

As further depicted in FIG. 8, the sulphuric acid plant generates steam that drives a turbine to produce electricity which is input to the grid as shown. Some of the electricity may be used to power an air separation unit (ASU) 10 which separates oxygen and nitrogen. The oxygen may be supplied to the sulphur submerged combustor. The nitrogen may be supplied to the ammonia plant.

The embodiments of the present invention confer a number of significant advantages and technical effects which reduce or eliminate many of the disadvantages of the prior art.

In some embodiments, the HES energy system are envisioned as sulphur cycles which become sources of energy and hydrogen where most of the $CO_2$ is recycled before it is used or sequestered.

In some embodiments, a solvent-based amine unit is not required to capture carbon dioxide from the flue gas. In some embodiments, $CO_2$ capture/separation from an influent is achieved by passing the $CO_2$-containing gas in intimate contact with carbon disulphide ($CS_2$), as an alternative to amine solvent, in the presence of a catalyst that is capable of facilitating the separation by conversion of $CO_2$ to COS.

Some embodiments of the present invention are directed to systems and methods in which the $SO_2$ from flue gases can be captured through a Flue Gas Desulphurisation (FGD) regenerable system producing concentrated $SO_2$ using regenerable sorbents and then catalytically reducing to COS.

According to yet another aspect of the present invention, there is provided a method of a sulphur thermochemical water splitting process at significant lower temperatures and reduced in complexity due to direct coupling $SO_2$-depolarized electrolyser (SDE) with Hybrid Energy System (HES) which will provides required thermal and electric energy and the same time enable curing out of the sulphur recycling.

Another aspect of the present invention is a method of generating COS by bringing petroleum coke into direct contact with heated gaseous sulfur dioxide to produce a gaseous mixture of carbon monoxide and elemental sulfur which is sequentially converted in the presence of a catalyst to carbonyl sulphide.

The present invention provides an innovative technique for efficiently sequestering carbon dioxide by converting the carbon dioxide to carbonyl sulphide for transport via a pipeline to a sequestration site where the carbon can be stored by injecting it as COS into the ground. Alternatively, carbon dioxide can be recovered from the COS and injected as carbon dioxide into the ground.

The present invention also provides innovative techniques for sulphur transport, storage and/or recovery. Sulphur-containing by-products of oil and gas production are converted to COS for transport and storage. COS can be transported at ambient temperatures through unheated pipelines without corrosion issues, thereby facilitating the transport of sulphur from extraction sites to market. Sulphur can be stored as COS rather than as elemental sulphur blocks which can be environmentally problematic. COS provides an efficient means to sequester large amounts of carbon while also storing sulphur in a desired location for future recovery. Sulphur can be recovered from the sulphur storage sites for combustion, manufacturing of sulphur-based products like sulphuric acid, or for transport to market. In other words, sulphur that is subsequently recovered from COS downstream of the pipeline may be combusted for energy generation, while the carbon dioxide obtained from recovering the sulphur from the COS can be separated and sequestered.

Thus, this invention provides a system and method for simultaneously conveying sulphur (S) and carbon dioxide ($CO_2$) to market, storage and/or sequestration sites by converting the sulphur and carbon dioxide into COS which is easier to transport via pipeline. In addition, the COS can be transported via ship, vessel, truck, train, or other transport or cargo vehicle capable of carrying a liquid or gas. In other words, this invention provides a process that takes carbon dioxide and sulphur (or sulphur compounds) and converts them to carbonyl sulphide (COS) which is easy, safe, and economical to transport as a liquid by pipeline, or any carrier, vessel or truck capable of transporting liquid.

Some embodiments of this invention may have particular utility for the oil sands or tar sands, specifically as a method of converting carbon dioxide and sulphur (or sulphur compounds) which are found in large quantities in the tar sands (or in sour oil and natural gas treatment plants) to carbonyl sulphide (COS).

This invention provides a method for utilization of carbon disulphide ($CS_2$) produced by the utilization of petroleum coke, and in particular oil-sands fluid coke.

In some embodiments of the invention, the method entails generating energy by utilization of sulphur dioxide ($SO_2$) that is generated by sulphur combustion and the utilization of oil-sands fluid coke to produce carbonyl sulphide (COS).

In some embodiments, the present invention further provides a method of sulphur recovery comprising the steps of (a) combusting sulphur to produce sulphur dioxide and heat energy; and (b) reacting the sulphur dioxide with carbonyl sulphide to produce elemental sulphur and carbon dioxide ready for sequestration. The heat energy produced by this process of sulphur recovery can be used for steam/power generation or, alternatively, for powering a sulphur-transport vessel or other vehicle carrying sulphur in the form of COS.

The present invention has been described in terms of specific embodiments, examples, implementations and configurations which are intended to be exemplary or illustrative only. Other variants, modifications, refinements and applications of this innovative technology will become readily apparent to those of ordinary skill in the art who have had the benefit of reading this disclosure. Such variants, modifications, refinements and applications fall within the ambit and scope of the present invention.

The invention claimed is:

1. A system for sulphur-assisted carbon capture and utilization, the system comprising:
   a sulphur depolarized electrolyser (SDE) for receiving electricity, $H_2O$ and $SO_2$ and for electrolysing the $H_2O$ and $SO_2$ to produce hydrogen and sulphuric acid ($H_2SO_4$);
   a decomposition reactor for receiving and decomposing the $H_2SO_4$ into $SO_3$ and $H_2O$, wherein the $H_2O$ is recycled to the SDE;
   a sulphur submerged combustor for converting the $SO_3$ to $SO_2$ and producing $S_n$ vapor;
   a sulphur power plant for combusting $S_n$ vapor to produce $SO_2$, electricity and heat and for supplying the $SO_2$ and the electricity to the SDE and for supplying the heat to the decomposition reactor;
   wherein the hydrogen is delivered to a carbon capture and utilization facility.

2. The system of claim 1 further comprising the carbon utilization facility which is configured to form fuel or chemicals by combining the hydrogen and carbon dioxide.

3. The system of claim 1 further comprising an evaporating reactor for concentrating the $H_2SO_4$ in addition to the decomposition reactor.

4. The system of claim 3 wherein the evaporating and decomposition reactors receive heat from a water-wall boiler.

5. The system of claim 4 wherein the water-wall boiler comprises a radiation zone and a catalytic reaction zone.

6. The system of claim 4 wherein the water-wall boiler receives $S_n$ and $SO_2$ from a sulphur submerged combustor fed by recycled sulphur from a sulphur condenser.

7. The system of claim 1 wherein the carbon utilization facility that receives the hydrogen is an ammonia plant.

8. The system of claim 1 wherein the ammonia plant receives nitrogen from an air separation unit powered by a steam turbine that receives heat from a sulphuric acid plant.

9. The system of claim 1 further comprising a urea plant and wherein the ammonia plant supplies $NH_3$ to the urea plant, wherein the urea plant also receives carbon dioxide from a power plant or industrial carbon-emitting facility.

10. The system of claim 1 further comprising a Flue Gas Desulphurisation (FGD) regenerable system for receiving a flue gas from a power or industrial facility and for removing $SO_2$ from the flue gas.

11. The system of claim 10 further comprising a $CO_2$ converter downstream of the FGD regenerable system for receiving the flue gas from the FGD regenerable system and for receiving $CS_2$ and for generating COS.

12. The system of claim 11 further comprising a separator downstream of the $CO_2$ converter for separating the COS from the flue gas.

13. A method of sulphur-assisted carbon capture and utilization, the method comprising:
receiving electricity, $H_2O$ and $SO_2$ at a sulphur depolarized electrolyser (SDE);
electrolysing the $H_2O$ and $SO_2$ to produce hydrogen and sulphuric acid ($H_2SO_4$);
receiving and decomposing the $H_2SO_4$ into $SO_3$ and $H_2O$;
recycling the $H_2O$ to the SDE;
converting using a sulphur submerged combustor the $SO_3$ to $SO_2$ and producing $S_n$ vapor;
combusting $S_n$ vapor to produce $SO_2$, electricity and heat;
supplying the $SO_2$ and the electricity to the SDE;
supplying the heat to the decomposition reactor;
delivering the hydrogen to a carbon capture and utilization facility.

14. The method of claim 13 further comprising, at the carbon capture and utilization facility, forming fuel or chemicals by combining the hydrogen and carbon dioxide.

15. The method of claim 14 further comprising concentrating the $H_2SO_4$ using an evaporating reactor.

16. The method of claim 15 comprising receiving heat at the evaporating and decomposition reactors from a water-wall boiler.

17. The method of claim 16 wherein the water-wall boiler comprises a radiation zone and a catalytic reaction zone.

18. The method of claim 16 comprising:
receiving, by the water-wall boiler, sulphur vapour from a sulphur submerged combustor; and
feeding the sulphur submerged combustor by recycling sulphur from a sulphur condenser.

19. The method of claim 13 comprising receiving the hydrogen at an ammonia plant.

20. The method of claim 13 comprising receiving nitrogen at the ammonia plant from an air separation unit powered by a steam turbine that receives heat from a sulphuric acid plant.

* * * * *